United States Patent
Ashton et al.

(10) Patent No.: US 7,238,683 B2
(45) Date of Patent: Jul. 3, 2007

(54) FUSED PHENYLALANINE DERIVATIVES AS DIPEPTIDYL PEPTIDASE-IV INHIBITORS FOR THE TREATMENT OR PREVENTION OF DIABETES

(75) Inventors: Wallace T. Ashton, Edison, NJ (US); Hong Dong, Livingston, NJ (US); Jinyou Xu, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/573,108

(22) PCT Filed: Oct. 29, 2004

(86) PCT No.: PCT/US2004/036252

§ 371 (c)(1),
(2), (4) Date: Mar. 23, 2006

(87) PCT Pub. No.: WO2005/044195

PCT Pub. Date: May 19, 2005

(65) Prior Publication Data

US 2006/0281727 A1  Dec. 14, 2006

Related U.S. Application Data

(60) Provisional application No. 60/517,287, filed on Nov. 4, 2003.

(51) Int. Cl.
| | |
|---|---|
| *C07D 207/04* | (2006.01) |
| *C07D 401/10* | (2006.01) |
| *C07D 403/10* | (2006.01) |
| *C07D 487/04* | (2006.01) |
| *A61K 31/40* | (2006.01) |
| *A61K 31/4439* | (2006.01) |
| *A61K 31/454* | (2006.01) |
| *A61K 31/437* | (2006.01) |
| *A61K 31/4985* | (2006.01) |
| *A61K 31/506* | (2006.01) |
| *A61K 31/4725* | (2006.01) |
| *A61P 3/10* | (2006.01) |

(52) U.S. Cl. .................. 514/210.17; 514/210.18; 514/249; 514/274; 514/319; 514/343; 514/423; 544/316; 544/350; 546/119; 546/205; 546/279.1; 546/141; 548/540; 548/953

(58) Field of Classification Search ............... 544/316, 544/350; 546/119, 205, 279.1; 548/540, 548/953; 514/210.17, 210.18, 249, 274, 514/319, 343, 423
See application file for complete search history.

(56) References Cited

U.S. PATENT DOCUMENTS

| | | | |
|---|---|---|---|
| 4,386,090 A | 5/1983 | Moinet et al. | |
| 5,939,560 A | 8/1999 | Jenkins et al. | |
| 6,011,155 A | 1/2000 | Villhauer | |
| 6,166,063 A | 12/2000 | Villhauer | |
| 6,303,661 B1 | 10/2001 | Demuth et al. | |
| 6,432,969 B1 | 8/2002 | Villhauer | |
| 6,699,871 B2 | 3/2004 | Edmondson et al. | |
| 6,812,350 B2 * | 11/2004 | Hulin | 548/540 |
| 7,026,316 B2 * | 4/2006 | Ashton et al. | 514/242 |
| 7,157,490 B2 * | 1/2007 | Colandrea et al. | 514/423 |
| 7,196,201 B2 * | 3/2007 | Haffner et al. | 548/200 |
| 2006/0111336 A1 * | 5/2006 | Duffy et al. | 514/210.17 |

* cited by examiner

*Primary Examiner*—Fiona T. Powers
(74) *Attorney, Agent, or Firm*—Philippe L. Durette; Catherine D. Fitch

(57) ABSTRACT

The present invention is directed to fused phenylalanine derivatives which are inhibitors of the dipeptidyl peptidase-IV enzyme ("DP-RV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

20 Claims, No Drawings

US 7,238,683 B2

FUSED PHENYLALANINE DERIVATIVES AS DIPEPTIDYL PEPTIDASE-IV INHIBITORS FOR THE TREATMENT OR PREVENTION OF DIABETES

CROSS REFERENCE TO RELATED APPLICATIONS

This application is the National Stage of International Application No. PCT/US2004/036252, filed 29 Oct. 2004, which claims the benefit under 35 U.S.C. 119(e) of U.S. Provisional Application No. 60/517,287, filed 4 Nov. 2003.

FIELD TO THE INVENTION

The present invention relates to novel fused phenylalanine derivatives which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4diones) are a more recently described class of compounds with potential for ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DP-IV" or "DPP-IV") enzyme are also under investigation as drugs that may be useful in the treatment of diabetes, and particularly type 2 diabetes. See for example WO 97/40832, WO 98/19998, U.S. Pat. No. 5,939,560, Bioorg. Med. Chem. Lett., 6: 1163-1166 (1996); and Bioorg. Med. Chem. Lett., 6: 2745-2748 (1996). The usefulness of DP-IV inhibitors in the treatment of type 2 diabetes is based on the fact that DP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DP-IV leads to decreased inactivation of the incretins, and this in turn results in increased effectiveness of the incretins in stimulating production of insulin by the pancreas. DP-IV inhibition therefore results in an increased level of serum insulin. Advantageously, since the incretins are produced by the body only when food is consumed, DP-IV inhibition is not expected to increase the level of insulin at inappropriate times, such as between meals, which can lead to excessively low blood sugar (hypoglycemia). Inhibition of DP-IV is therefore expected to increase insulin without increasing the risk of hypoglycemia, which is a dangerous side effect associated with the use of insulin secretagogues.

DP-IV inhibitors also have other therapeutic utilities, as discussed herein. DP-IV inhibitors have not been studied extensively to date, especially for utilities other than diabetes. New compounds are needed so that improved DP-IV inhibitors can be found for the treatment of diabetes and potentially other diseases and conditions. The therapeutic potential of DP-IV inhibitors for the treatment of type 2 diabetes is discussed by D. J. Drucker in *Exp. Opin. Invest. Drugs,* 12: 87-100 (2003) and by K. Augustyns, et al., in *Exp. Opin. Ther. Patents,* 13: 499-510 (2003).

SUMMARY OF THE INVENTION

The present invention is directed to novel fused phenylalanine derivatives which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatnent of such diseases in which the dipeptidyl peptidase-IV enzyme is involved.

DETAILED DESCRIPTION OF THE INVENTION

The present invention relates to fused phenylalanine derivatives useful as inhibitors of dipeptidyl peptidase-IV. Compounds of the present invention are described by structural formula I:

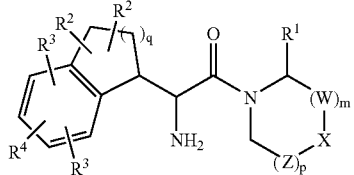

(I)

or a pharmaceutically acceptable salt thereof; wherein
each n is independently 0, 1, or 2;
m and p are each independently 0 or 1;
q is 1 or 2;
X is $CH_2$, S, SO, $SO_2$, CHF, or $CF_2$;
W and Z are each independently $CH_2$, CHF, or $CF_2$;
$R^1$ is hydrogen or cyano;
each $R^2$ is independently selected from the group consisting of hydrogen, halogen, $C_{1-4}$ alkyl, $C_{1-4}$ alkoxy, trifluoromethyl, trifluoromethoxy, and hydroxy;
each $R^3$ is independently selected from the group consisting of hydrogen, halogen, $C_{1-4}$ alkyl, $C_{1-4}$ alkoxy, trifluoromethyl, trifluoromethoxy, and hydroxy;
$R^4$ is hydrogen, halogen, aryl, heteroaryl, or heterocyclyl, wherein aryl, heteroaryl, and heterocyclyl are unsubstituted or substituted with one to five $R^5$ substituents;
each $R^5$ is independently selected from the group consisting of
halogen,
cyano,
oxo,
hydroxy,
$C_{1-6}$ alkyl, wherein alkyl is unsubstituted or substituted with one to five halogens,
$C_{1-6}$ alkoxy, wherein alkoxy is unsubstituted or substituted with one to five halogens,
$(CH_2)_n$—$NR^6R^7$,
$(CH_2)_n$—$CONR^6R^7$,
$(CH_2)_n$—$OCONR^6R^7$,
$(CH_2)_n$—$SO_2NR^6R^7$,
$(CH_2)_n$—$SO_2R^9$,
$(CH_2)_n$—$NR^8SO_2R^9$,
$(CH_2)_n$—$NR^8CONR^6R^7$,
$(CH_2)_n$—$NR^8COR^8$,
$(CH_2)_n$—$NR^8CO_2R^9$,
$(CH_2)_n$—COOH,
$(CH_2)_n$—$COOC_{1-6}$ alkyl,
$(CH_2)_n$-aryl, wherein aryl is unsubstituted or substituted with one to five substituents independently selected from halogen, hydroxy, $CO_2H$, $C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens,
$(CH_2)_n$-heteroaryl, wherein heteroaryl is unsubstituted or substituted with one to three substituents independently selected from hydroxy, halogen, $CO_2H$, $C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens,
$(CH_2)_n$-heterocyclyl, wherein heterocyclyl is unsubstituted or substituted with one to three substituents independently selected from oxo, hydroxy, halogen, $CO_2H$, $C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens,
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens,
wherein any methylene ($CH_2$) carbon atom in $R^5$ is unsubstituted or substituted with one to two groups independently selected from halogen, hydroxy, and $C_{1-4}$ alkyl unsubstituted or substituted with one to five halogens;
$R^6$ and $R^7$ are each independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five substituents independently selected from halogen and hydroxy and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
or $R^6$ and $R^7$ together with the nitrogen atom to which they are attached form a heterocyclic ring selected from azetidine, pyrrolidine, piperidine, piperazine, and morpholine wherein said heterocyclic ring is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens; and
each $R^9$ is independently selected from the group consisting of tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, and wherein any methylene ($CH_2$) carbon atom in $R^9$ is unsubstituted or substituted with one to two groups independently selected from halogen, hydroxy, and $C_{1-4}$ alkyl unsubstituted or substituted with one to five halogens; and each $R^8$ is hydrogen or $R^9$.

In one embodiment of the compounds of the present invention, the carbon atom marked with an * has the stereochemical configuration as depicted in formula Ia:

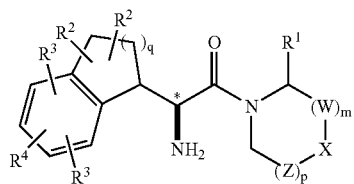
(Ia)

wherein $R^2$ and $R^3$ are each independently hydrogen or fluorine; and

W, X, Z, m, p, q, $R^1$, and $R^4$ are as defined above.

In a class of this embodiment of the compounds of the present invention, the carbon atom attached to $R^1$ marked with an ** has the stereochemical configuration as depicted in the formula Ib:

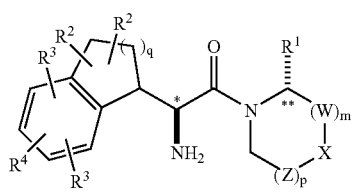
(Ib)

wherein $R^2$ and $R^3$ are each independently hydrogen or fluorine, and

W, X, Z, m, p, q, $R^1$, and $R^4$ are as defined above.

In a second embodiment of the compounds of the present invention, m is 1 and p is 0 as depicted in formula Ic:

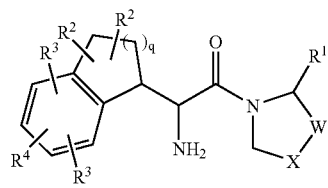
(Ic)

wherein $R^2$ and $R^3$ are each independently hydrogen or fluorine, and

W, X, q, $R^1$, and $R^4$ are as defined above.

A class of this embodiment encompasses compounds wherein the carbon atom marked with an * and the carbon atom marked with an ** have the stereochemical configurations as depicted in the formula Id:

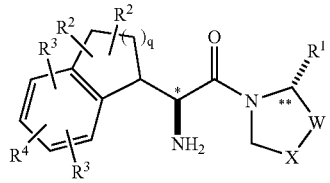
(Id)

wherein $R^2$ and $R^3$ are each independently hydrogen or fluorine, and W, X, q, $R^1$, and $R^4$ are as defined above.

In a subclass of this class of the compounds of the present invention, $R^1$ is hydrogen; W is $CH_2$; and X is $CH_2$, CHF or $CF_2$.

In a third embodiment of the compounds of the present invention, $R^1$ is hydrogen, X is CHF, and m and p are 0 as depicted in the formula Ie:

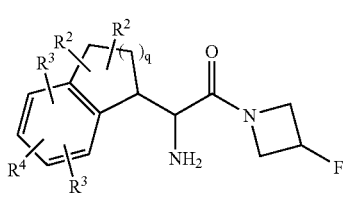
(Ie)

wherein $R^2$ and $R^3$ are each independently hydrogen or fluorine, and q and $R^4$ are as defined above.

A class of this embodiment encompasses compounds wherein the carbon atom marked with an * has the stereochemical configuration as depicted in the formula If:

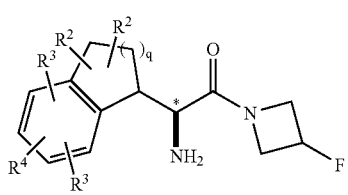
(If)

wherein $R^2$ and $R^3$ are each independently hydrogen or fluorine, and q and $R^4$ are as defined above.

A fourth embodiment of the present invention encompasses compounds of structural formula Ig:

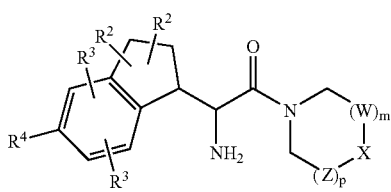
(Ig)

wherein q is 1; $R^2$ and $R^3$ are each independently hydrogen or fluorine; and W, X, Z, m, p, and $R^4$ are as defined above.

A class of this fourth embodiment encompasses compounds wherein the carbon atom marked with an * has the stereochemical configuration as depicted in the formula Ih:

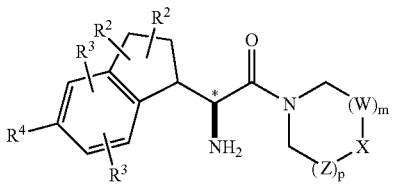

(Ih)

wherein $R^2$ and $R^3$ are each independently hydrogen or fluorine, and W, X, Z, m, p, and $R^4$ are as defined above.

Another class of this fourth embodiment encompasses compounds wherein the carbon atom marked with an * and the carbon atom marked with an *** have the stereochemical configurations as depicted in the formula Ii:

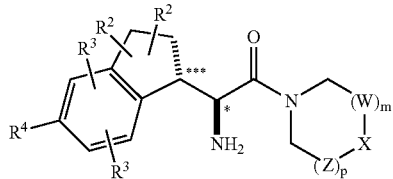

(Ii)

wherein $R^2$ and $R^3$ are each independently hydrogen or fluorine, and W, X, Z, m, p, and $R^4$ are as defined above.

In a subclass of this class of the fourth embodiment, X is $CH_2$, S, CHF, or $CF_2$;

W and Z are each independently $CH_2$, CHF, or $CF_2$;

$R^4$ is halogen, phenyl, heteroaryl, or heterocyclyl, wherein phenyl, heteroaryl, and heterocyclyl are unsubstituted or substituted with one to three $R^5$ substituents; and each $R^5$ is independently selected from the group consisting of:
halogen,
cyano,
oxo,
hydroxy,
$C_{1-6}$ alkyl, wherein alkyl is unsubstituted or substituted with one to five halogens,
$C_{1-6}$ alkoxy, wherein alkoxy is unsubstituted or substituted with one to five halogens,
$NR^6R^7$,
$CONR^6R^7$,
$OCONR^6R^7$,
$SO_2NR^6R^7$,
$SO_2R^9$,
$NR^8SO_2R^9$,
$NR^8CONR^6R^7$,
$NR^8COR^8$,
$NR8CO_2R_9$,
COOH,
$COOC_{1-6}$alkyl,
aryl, wherein aryl is unsubstituted or substituted with one to five substituents independently selected from halogen, hydroxy, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
heteroaryl, wherein heteroaryl is unsubstituted or substituted with one to three substituents independently selected from hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
heterocyclyl, wherein heterocyclyl is unsubstituted or substituted with one to three substituents independently selected from oxo, hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens, and
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens.

In a subclass of this subclass, each $R^5$ is independently selected from the group consisting of:
halogen,
oxo,
$C_{1-6}$ alkyl, wherein alkyl is unsubstituted or substituted with one to five halogens,
$C_{1-6}$ alkoxy, wherein alkoxy is unsubstituted or substituted with one to five halogens, and
$C_{3-6}$ cycloalkyl.

In a further subclass of this subclass, $R^4$ is selected from the group consisting of:
bromo,
4-fluorophenyl,
2-methoxyphenyl,
1-methylpiperidin-2-on-5-yl,
1-methylpyridin-2(1H)-on-5-yl,
[1,2,4]triazolo[4,3-α]pyridin-6-yl,
3-(cyclopropyl)[1,2,4]triazolo[4,3-α]pyridin-6-yl,
[1,2,4]triazolo[1,5-α]pyridin-6-yl,
[1,2,4]triazolo[1,5-α]pyridin-7-yl,
[1,2,4]triazolo[1,5-α]pyrazin-5-yl,
2-(trifluoromethyl)[1,2,4]triazolo[1,5-α]pyrazin-5-yl, and
1-methylpyrimidin-2(1H)-on-5-yl.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-10}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-10}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl (MeSo$_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocycle" and "heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazoildine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

"Heteroaryl" means an aromatic or partially aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-(1H)-pyridinyl (2-hydroxy-pyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-α]pyridinyl, [1,2,4-triazolo][4,3-α]pyridinyl, pyrazolo[1,5-α]pyridinyl, [1,2,4triazolo] [1,5-α]pyridinyl, 2-oxo-1,3-benzoxazolyl, 4-oxo-3H-quinazolinyl, 3-oxo-[1,2,4]-triazolo[4,3-α]-2H-pyridinyl, 5-oxo-[1,2,4]4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The compounds of the present invention may contain one or more asymmetric centers and can thus occur as racemates and racemic mixtures, single enantiomers, diastereomeric mixtures and individual diastereomers. In particular the compounds of the present invention have an asymmetric center at the carbon atom marked with an * in formulae Ia, If, and Ih, at the carbon atoms marked with an * and ** in formulae Ib and Id, and at the carbon atoms marked with an * and *** in formula Ii. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

Formula I shows the structure of the class of compounds without preferred stereochemistry. Formula Ia shows the preferred stereochemistry at the carbon atom to which is attached the amino group of the alpha-amino acid from which these compounds are prepared. Formula Ib shows the preferred stereochemistry at the carbon atom to which is attached the amino group of the alpha-amino acid from which these compounds are prepared and at the stereogenic carbon atom to which the $R^1$ substituent is attached. Formula Ii shows the preferred stereochemistry at the carbon atom to which is attached the amino group of the alpha-amino acid from which these compounds are prepared and at the stereogenic carbon atom of the fused indanyl moiety marked with an ***.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

Solvates, and in particular, the hydrates of the compounds of structural formula I are included in the present invention as well.

Exemplifying the invention is the use of the compounds disclosed in the Examples and herein.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutically acceptable carrier or diluent.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DP-IV to release the fluorescent AMC leaving group. The kinetic parameters that describe this reaction are as follows: $K_m=50$ µM; $k_{cat}=75$ s$^{-1}$; $k_{cat}/K_m=1.5\times10^6$ M$^{-1}$s$^{-1}$. A typical reaction contains approximately 50 pM enzyme, 50 µM Gly-Pro-AMC, and buffer (100 mM HEPES, pH 7.5, 0.1 mg/ml BSA) in a total reaction volume of 100 µl. Liberation of AMC is monitored continuously in a 96-well plate fluorometer using an excitation wavelength of 360 nm and an emission wavelength of 460 nm. Under these conditions, approximately 0.8 µM AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

In particular, the compounds of the following examples had activity in inhibiting the dipeptidyl peptidase-IV enzyme in the aforementioned assays, generally with an $IC_{50}$ of less than about 1 µM. Such a result is indicative of the intrinsic activity of the compounds in use as inhibitors the dipeptidyl peptidase-IV enzyme activity.

Dipeptidyl peptidase-IV enzyme (DP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DP-IV is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions:

Type II Diabetes and Related Disorders: It is well established that the incretins GLP-1 and GIP are rapidly inactivated in vivo by DP-IV. Studies with DP-IV$^{(-/-)}$-deficient mice and preliminary clinical trials indicate that DP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DP-IV (eg. PACAP). Inactivation of these peptides by DP-IV may also play a role in glucose homeostasis. The DP-IV inhibitors of the present invention therefore have utility in the treatment of type II diabetes and in the treatment and prevention of the numerous conditions that often accompany Type II diabetes, including Syndrome X (also known as Metabolic Syndrome), reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, DP-IV inhibitors may also be useful to treat hypertension associated with this condition.

Obesity: DP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (*Am. J. Physiol.*, 277: R910-R916 (1999)). ICV administration of GLP-1 in rats and mice also has profound effects on food intake (*Nature Medicine*. 2: 1254-1258 (1996)). This inhibition of feeding is not observed in GIP-1R$^{(-/-)}$ mice, indicating that these effects are mediated through brain GLP-1 receptors. By analogy to GLP-1, it is likely that GLP-2 is also regulated by DP-IV. ICV administration of GLP-2 also inhibits food intake, analogous to the effects observed with GLP-1 (*Nature Medicine*, 6: 802-807 (2000)). In addition, studies with DP-IV deficient mice suggest that these animals are resistant to diet-induced obesity and associated pathology (e.g. hyperinsulinonemia).

Growth Hormone Deficiency: DP-IV inhibition may be useful for the treatment of growth hormone deficiency, based on the hypothesis that growth-hormone releasing factor (GRF), a peptide that stimulates release of growth hormone from the anterior pituitary, is cleaved by the DP-IV enzyme in vivo (WO 00/56297). The following data provide evidence that GRF is an endogenous substrate: (1) GRF is efficiently cleaved in vitro to generate the inactive product GRF[3-44] (*BBA* 1122: 147-153 (1992)); (2) GRP is rapidly degraded in plasma to GRF[3-44]; this is prevented by the DP-IV inhibitor diprotin A; and (3) GRF[3-44] is found in the plasma of a human GRB transgenic pig (*J. Clin. Invest.*, 83: 1533-1540 (1989)). Thus DP-IV inhibitors may be useful for the same spectrum of indications which have been considered for growth hormone secretagogues.

Intestinal Injury: The potential for using DP-IV inhibitors for the treatment of intestinal injury is suggested by the results of studies indicating that glucagon-like peptide-2 (GLP-2), a likely endogenous substrate for DP-IV, may exhibit trophic effects on the intestinal epithelium (*Regulator Peptides*, 90: 27-32 (2000)). Administration of GLP-2 results in increased small bowel mass in rodents and attenuates intestinal injury in rodent models of colitis and enteritis.

Immunosuppression: DP-IV inhibition may be useful for modulation of the immune response, based upon studies implicating the DP-IV enzyme in T cell activation and in chemokine processing, and efficacy of DP-IV inhibitors in in vivo models of disease. DP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DP-IV. In several cases (RANTES, ID78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DP-IV hydrolysis.

DP-IV inhibitors have been shown to be efficacious immunosuppressants in animal models of transplantation and arthritis. Prodipine (Pro-Pro-diphenyl-phosphonate), an irreversible inhibitor of DP-IV, was shown to double cardiac allograft survival in rats from day 7 to day 14 (*Transplantation*, 63: 1495-1500 (1997)). DP-IV inhibitors have been tested in collagen and alkyldiamine-induced arthritis in rats and showed a statistically significant attenuation of hind paw swelling in this model [*Int. J. Immunopharmacology*, 19:15-24 (1997) and *Immunopharmacology*, 40: 21-26 (1998)]. DP-IV is upregulated in a number of autoimmune diseases including rheumatoid arthritis, multiple sclerosis, Graves' disease, and Hashimoto's thyroiditis (*Immunology Today*, 20: 367-375 (1999)).

HIV Infection: DP-IV inhibition may be useful for the treatment or prevention of HIV infection or AIDS because a number of chemokines which inhibit HIV cell entry are potential substrates for DP-IV (*Immunology Today* 20: 367-375 (1999)). In the case of SDF-1alpha, cleavage decreases antiviral activity (*PNAS*, 95: 6331-6 (1998)). Thus, stabilization of SDF-1alpha through inhibition of DP-IV would be expected to decrease HIV infectivity.

Hematopoiesis: DP-IV inhibition may be useful for the treatment or prevention of hematopiesis because DP-IV may be involved in hematopoiesis. A DP-IV inhibitor, Val-Boro-Pro, stimulated hematopoiesis in a mouse model of cyclophosphamide-induced neutropenia (WO 99/56753).

Neuronal Disorders: DP-IV inhibition may be useful for the treatment or prevention of various neuronal or psychiatric disorders because a number of peptides implicated in a variety of neuronal processes are cleaved in vitro by DP-IV. A DP-IV inhibitor thus may have a therapeutic benefit in the treatment of neuronal disorders. Endomorphin-2, beta-casomorphin, and substance P have all been shown to be in vitro substrates for DP-IV. In all cases, in vitro cleavage is highly efficient, with $k_{cat}/K_m$ about $10^6$ $M^{-1}s^{-1}$ or greater. In an electric shock jump test model of analgesia in rats, a DP-IV inhibitor showed a significant effect that was independent of the presence of exogenous endomorphin-2 (*Brain Research*, 815: 278-286 (1999)). Neuroprotective and neuroregenerative effects of DP-IV inhibitors were also evidenced by the inhibitors' ability to protect motor neurons from excitotoxic cell death, to protect striatal innervation of dopaminergic neurons when administered concurrently with MPTP, and to promote recovery of striatal innervation density when given in a therapeutic manner following MPTP treatment [see Yong-Q. Wu, et al., "Neuroprotective Effects of Inhibitors of Dipeptidyl Peptidase-IV In Vitro and In Vivo," *Int. Conf. On Dipeptidyl Aminopeptidases: Basic Science and Clinical Applications*, Sep. 26-29, 2002 (Berlin, Germany)].

Anxiety

Rats naturally deficient in DP-IV have an anxiolytic phenotype (WO 02/34243; Karl et al., *Physiol. Behav.* 2003). DP-IV deficient mice also have an anxiolytic phenotype using the porsolt and light/dark models. Thus DP-IV inhibitors may prove useful for treating anxiety and related disorders.

Memory and Cognition

GLP-1 agonists are active in models of learning (passive avoidance, Morris water maze) and neuronal injury (kainate-induced neuronal apoptosis) as demonstrated by During et al. (*Nature Med.* 9: 1173-1179 (2003)). The results suggest a physiological role for GLP-1 in learning and neuroprotection. Stabilization of GLP-1 by DP-IV inhibitors are expected to show similar effects Tumor Invasion and Metastasis: DP-IV inhibition may be useful for the treatment or prevention of tumor invasion and metastasis because an increase or decrease in expression of several ectopeptidases including DP-IV has been observed during the transformation of normal cells to a malignant phenotype (*J. Exp. Med.*, 190: 301-305 (1999)). Up- or down-regulation of these proteins appears to be tissue and cell-type specific. For example, increased CD26/DP-IV expression has been observed on T cell lymphoma, T cell acute lymphoblastic leukemia, cell-derived thyroid carcinomas, basal cell carcinomas, and breast carcinomas. Thus, DP-IV inhibitors may have utility in the treatment of such carcinomas.

Benign Prostatic Hypertrophy: DP-IV inhibition may be useful for the treatment of benign prostatic hypertrophy because increased DP-IV activity was noted in prostate tissue from patients with BPH (*Eur. J. Clin. Chem. Clin. Biochem.*, 30: 333-338 (1992)).

Sperm motility/male contraception: DP-IV inhibition may be useful for the altering sperm motility and for male contraception because in seminal fluid, prostatosomes, prostate derived organelles important for sperm motility, possess very high levels of DP-IV activity (*Eur. J. Clin. Chem. Clin. Biochem.*, 30: 333-338 (1992)).

Gingivitis: DP-IV inhibition may be useful for the treatment of gingivitis because DP-IV activity was found in gingival crevicular fluid and in some studies correlated with periodontal disease severity (*Arch. Oral Biol.*, 37: 167-173 (1992)).

Osteoporosis: DP-IV inhibition may be useful for the treatment or prevention of osteoporosis because GIP receptors are present in osteoblasts.

The compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type II diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, and other conditions that may be treated or prevented by inhibition of DP-IV.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (D)P-IV) inhibitors;

(b) insulin sensitizers including (i) PPARγ agonists such as the glitazones (e.g. troglitazone, pioglitazone, englitazone, MCC-555, rosiglitazone, balaglitazone, and the like) and other PPAR ligands, including PPARα/γ dual agonists, such as KRP-297 and muraglitazar, and PPARα agonists such as fenofibric acid derivatives (gemfibrozil, clofibrate, fenofibrate and bezafibrate), (ii) biguanides such as metformin and phenformin, and (iii) protein tyrosine phosphatase-1B (PIP-1B) inhibitors;

(c) insulin or insulin mimetics;

(d) sulfonylureas and other insulin secretagogues, such as tolbutamide glyburide, glipizide, glimepiride, and meglitinides, such as nateglinide and repaglinide;

(e) α-glucosidase inhibitors (such as acarbose and miglitol);

(f) glucagon receptor antagonists such as those disclosed in WO 98/04528, WO 99/01423, WO 00/39088, and WO 00/69810;

(g) GLP-1, GLP-1 mimetics, such as Exendin 4, and liraglutide, and GLP-1 receptor agonists such as those disclosed in WO00/42026 and WO00/59887;

(h) GEP and GIP mimetics such as those disclosed in WO00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as KRP-297, (vi) inhibitors of cholesterol absorption, such as beta-sitosterol and ezetimibe, (vii) acyl CoA:cholesterol acyltransferase inhibitors, such as avasimibe, and (viii) anti-oxidants, such as probucol;

(k) PPARδ agonists, such as those disclosed in WO97/28149;

(l) antiobesity compounds such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin-receptor agonists, in particular melanocortin-4 receptor agonists, ghrelin antagonists, and melanin-concentrating hormone (MCH) receptor antagonists;

(m) ileal bile acid transporter inhibitors;

(n) agents intended for use in inflammatory conditions such as aspirin, non-steroidal anti-inflammatory drugs, glucocorticoids, azulfidine, and selective cyclooxygenase-2 inhibitors;

(o) antihypertensive agents such as ACE inhibitors (enalapril, lisinopril, captopril, quinapril, tandolapril), A-II receptor blockers (losartan, candesartan, irbesartan, valsartan, telmisartan, eprosartan), beta blockers and calcium channel blockers; and (p) glucokinase activators (GKAs).

Dipeptidyl peptidase-IV inhibitors that can be combined with compounds of structural formula I include those disclosed in WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); and WO 03/000181 (3 Jan. 2003). Specific DP-IV inhibitor compounds include isoleucine thiazolidide; NVP-DPP728; P32/98; and LAP 237.

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001) and D. Spanswick and K. Lee, "Emerging antiobesity drugs," *Expert Opin. Emerging Drugs*, 8: 217-237 (2003).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; and U.S. Pat. No. 5,292,736.

Melanocortin receptor agonists that can be combined with compounds of structural formula I include those disclosed in WO 03/009847 (6 Feb. 2003); WO 02/068388 (6 Sep. 2002); WO 99/64002 (16 Dec. 1999); WO 00/74679 (14 Dec. 2000); WO 01/70708 (27 Sep. 2001); and WO 01/70337 (27 Sep. 2001) as well as those disclosed in J. D. Speake et al., "Recent advances in the development of melanocortin-4 receptor agonists," *Expert Opin. Ther. Patents*, 12: 1631-1638 (2002).

The potential utility of safe and effective activators of glucokinase (GKAs) for the treatment of diabetes is discussed in J. Grimsby et al., "Allosteric Activators of Glucokinase: Potential Role in Diabetes Therapy," *Science*, 301: 370-373 (2003).

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention can be prepared from alpha-amino acid intermediates such as those of formula II and substituted heterocyclic intermediates such as those of formula III, using standard peptide coupling conditions followed by deprotection,

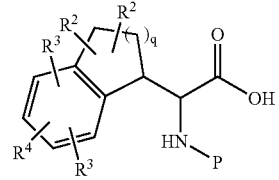

II

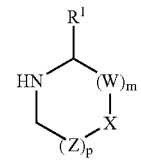

III where m, p, q, W, X, Z, $R^1$, $R^2$, $R^3$ and $R^4$ are as defined above and P is a suitable nitrogen protecting group such as tert-butoxycarbonyl (BOC), benzyloxycarbonyl (Cbz), or 9-fluorenylmethoxycarbonyl (Fmoc).

The preparation of these intermediates is described in the following Schemes.

SCHEME 1

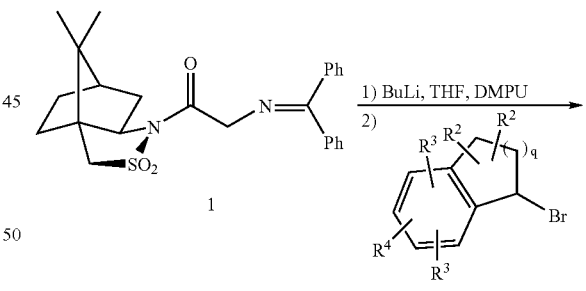

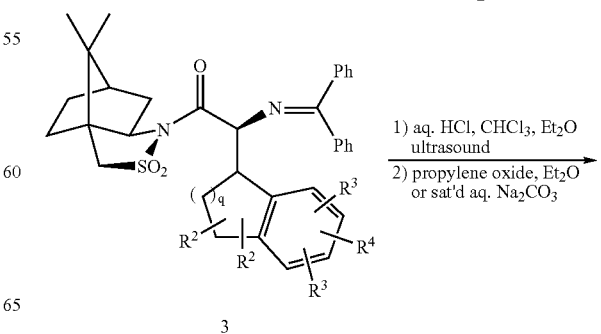

-continued

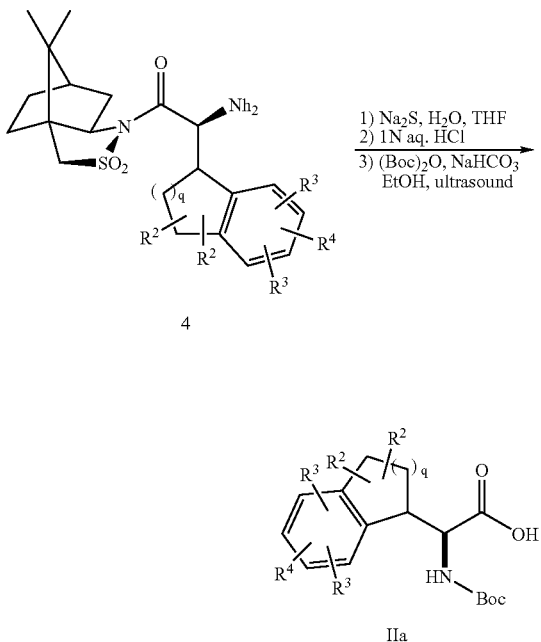

1) Na₂S, H₂O, THF
2) 1N aq. HCl
3) (Boc)₂O, NaHCO₃
   EtOH, ultrasound

4

IIa

Compounds of formula II are commercially available, known in the literature, or may be conveniently prepared by a variety of methods familiar to those skilled in the art. One common method involves the alkylation of a glycine enolate equivalent with an appropriate halide. Scheme 1 illustrates one convenient method to prepare enantiomerically pure amino acid IIa. Sultam glycinate 1 (H. Josien et al., *J. Med. Chem.*, 37, 1586 (1994)) is deprotonated, for example by treatment with n-butyllithium in a solvent system such as THF/DMPU at low temperature according to literature procedures (H. Josien et al., *J. Med. Chem.*, 37, 1586 (1994); W. Oppolzer et al., *Helv. Chim. Acta*, 77, 2363 (1994)). The resultant lithium enolate is alkylated with bromide 2 to provide 3 as a mixture of diastereomers, which may be separated chromatographically or by crystallization. Hydrolysis of the imine may be achieved by treatment with hydrogen chloride, conveniently in chloroform and ether using ultrasonification, followed by stifling with propylene oxide in ether or with saturated aqueous sodium carbonate to give amine 4. The sultam is removed with sodium sulfide in aqueous TBF or by other methods known in the literature. Protection of the amine, for example, as its BOC derivative may be effected using di-tert-butyl dicarbonate to give acid IIa (P=BOC). Alternate routes to the protected alpha-amino acid intermediates II can be found in the following articles and reviews: G. Li et al., *J. Chem. Soc. Perkin Trans.* 1, 3057 (1994); F.-D. Lung et al., *Synth. Commun.*, 25, 57 (1995); S. Liao et al., *Tetrahedron*, 53, 16645 (1997); R. M. Williams, *Advances in Asymmnetric Synthesis*, 1, 45 (1995); V. J. Hruby and X. Qian, *Methods in Molecular Biology*, 35 ("Peptide Synthesis Protocols"), 249 (1994); R. O. Duthaler, *Tetrahedron*, 50, 1539 (1994); A. Haemers et al., *Pharmazie*, 44, 97 (1989); K. Maruoka and T. Ooi, *Chem. Rev.*, 103, 3013 (2003); Taggi, A. E. et al., 36, 10 (2003); M. G. Natchu and X. Tian, *Organic Synthesis: Theory and Applications*, 5, 89 (2001); T. Abellan et al., *Eur. J. Org. Chem.*, 2689 (2000).

SCHEME 2

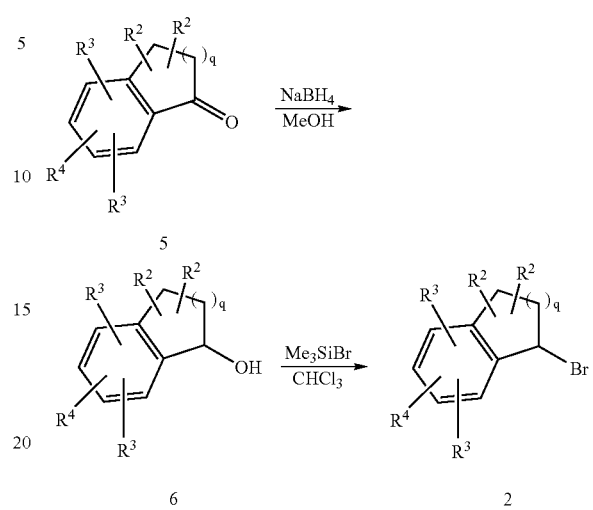

NaBH₄
MeOH

Me₃SiBr
CHCl₃

6                                2

Bromo derivatives 2 are commercially available, known in the literature, or may be conveniently prepared by a variety of methods familiar to those skilled in the art. One such method is shown in Scheme 2. Ketone derivative 5 is reduced to alcohol 6, for example by treatment with sodium borohydride in a solvent such as methanol. Conversion to the desired bromide 2 may be achieved by treating alcohol 6 with a brominating agent such as trimethylsilyl bromide, conveniently in chloroform at ambient temperature.

SCHEME 3

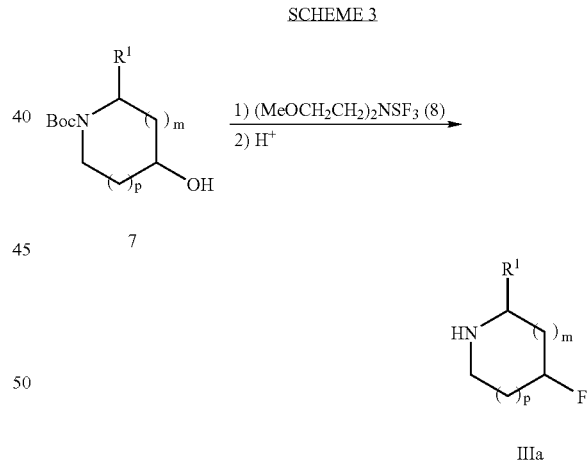

1) (MeOCH₂CH₂)₂NSF₃ (8)
2) H⁺

7

IIIa

Compounds of formula III are commercially available, known in the literature, or may be conveniently prepared by a variety of methods familiar to those skilled in the art. One convenient method for the preparation of intermediate IIIa, wherein X is CHF and W and Z are CH₂, is shown in Scheme 3. An appropriately protected alcohol 7, which itself is known in the literature or may be conveniently prepared by a variety of methods familiar to those skilled in the art, is treated with a fluorinating reagent such as (diethylamino) sulfur trifluoride (DAST) or [bis(2-methoxyethyl)amino] sulfur trifluoride (8) to provide, after deprotection, the fluoro intermediate IIIa.

SCHEME 4

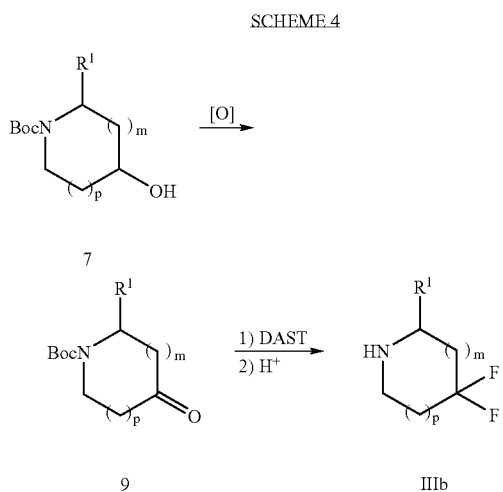

A method for the preparation of intermediate IIIb, wherein X is $CF_2$ and W and Z are $CH_2$, is shown in Scheme 4. An appropriately protected alcohol 7 is oxidized to the corresponding ketone 9 by a variety of methods known to those skilled in the art. Ketone 9 is treated with a fluorinating reagent, such as DAST, to provide, after deprotection, the fluoro intermediate IIIb.

SCHEME 5

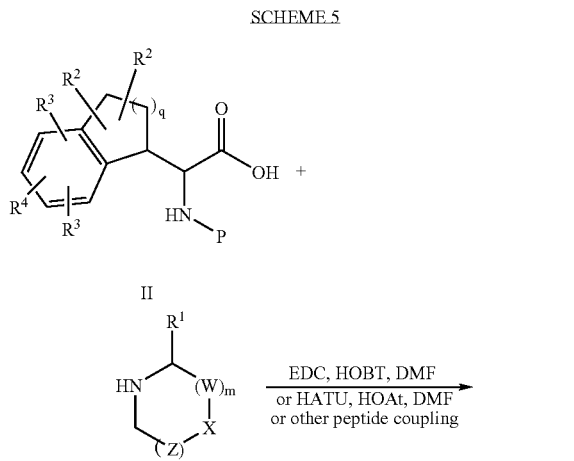

Intermediates II and III are coupled under standard peptide coupling conditions, for example, using 1-ethyl-3-(3-dimethylaminopropyl)carbodiimide and 1-hydroxybenzotriazole (DC/HOBT) or O-(7-azabenzotriazol-1-yl)-N,N,N', N'-tetramethyluronium hexafluorophosphate and 1-hydroxy-7-azabenzotriazole (HATU/HOAT) in a solvent such as N,N-dimethylformamide (DMF) or dichloromethane for 3 to 48 hours at ambient temperature to provide Intermediate 10 as shown in Scheme 5. In some cases, Intermediate III may be a salt, such as a hydrochloride or trifluoroacetic acid salt, and in these cases it is convenient to add a base, generally N,N-diisopropylethylamine, to the coupling reaction. The protecting group is then removed with, for example, trifluoroacetic acid or anhydrous hydrogen chloride in dioxane or methanol in the case of Boc to give the desired amine I. The product is purified from unwanted side products, if necessary, by recrystallization, trituration, preparative thin layer chromatography, flash chromatography on silica gel, such as with a Biotage® apparatus, or HPLC. Compounds that are purified by HPLC may be isolated as the corresponding salt. Purification of intermediates is achieved in the same manner.

In some cases intermediate 10 or product I, prepared as described in Scheme 5, may be further modified, for example, by manipulation of substituents $R^2$, $R^3$, or $R^4$. These manipulations may include, but are not limited to, reduction, oxidation, alkylation, acylation, and hydrolysis reactions which are commonly known to those skilled in the art.

SCHEME 6

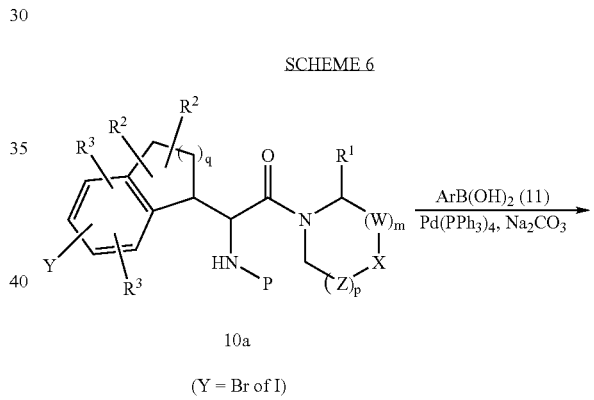

(Ar = appropriately substituted aryl, heteroaryl, or heterocyclyl)

One such example is illustrated in Scheme 6. Intermediate 10a, wherein $R^4$ is a halogen such as bromide and iodide, is coupled to boronic acid 11 in the presence of a palladium catalyst under Suzuki conditions to provide intermediate 10b. This is converted to product I as described in Scheme 5.

SCHEME 7

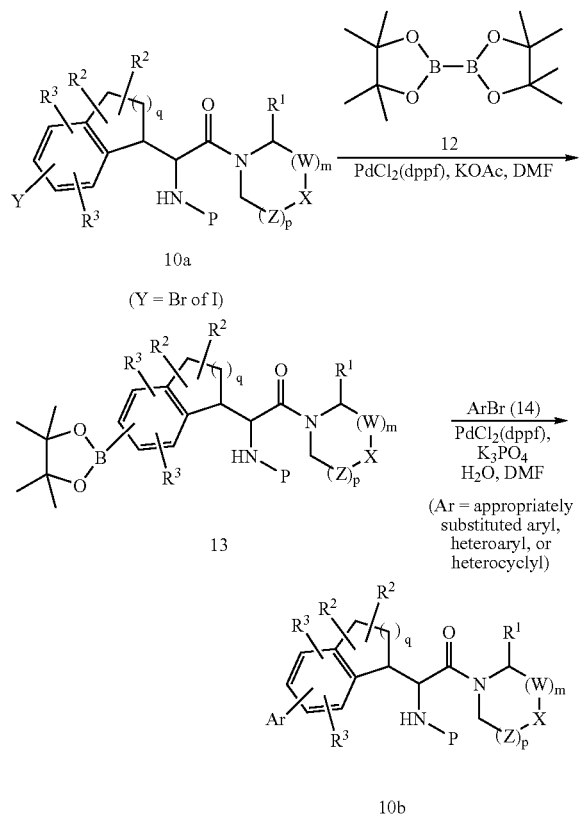

10a (Y = Br of I)

13

(Ar = appropriately substituted aryl, heteroaryl, or heterocyclyl)

10b

Another such example is illustrated in Scheme 7. Intermediate 10a is converted to the corresponding boronate ester 13. Boronate 13 may undergo Suzuki coupling with an appropriate halide, such as ArBr 14, in the presence of a palladium catalyst to provide the biaryl derivative 10b. This is converted to product I as described in Scheme 6.

SCHEME 8

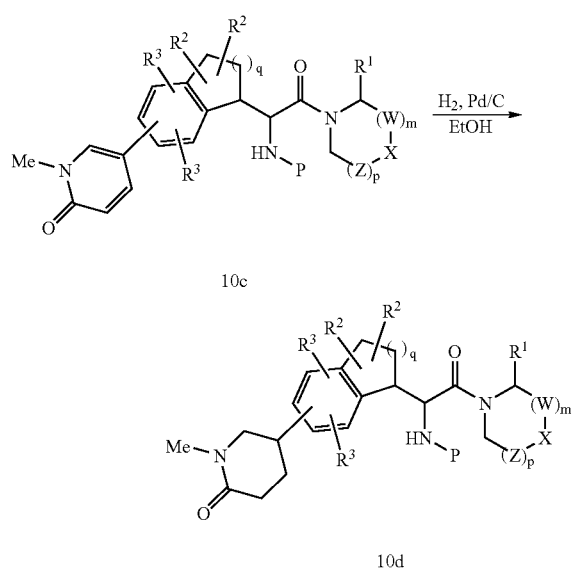

10c

10d

Scheme 8 illustrates an example in which the $R^4$ substituent undergoes further reaction. Hydrogenation of intermediate 10c, wherein $R^4$ is 1-methyl-6-oxo-piperidin-3-yl, provides the saturated derivative 10d. Intermediate 10d may be converted to product I as illustrated in Scheme 5.

In some cases the order of carrying out the foregoing reaction schemes may be varied to facilitate the reaction or to avoid unwanted reaction products. The following Examples are provided so that the invention might be more fully understood. These Examples are illustrative only and should not be construed as limiting the invention in any way.

Intermediate 1

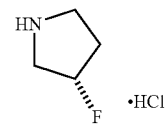

(3S)-3-Fluoropyrrolidine hydrochloride

Step A: Benzyl (3R)-3-hydroxypyrrolidine-1-carboxylate

A 22-L, 3-neck, round bottom flask equipped with mechanical stirrer, thermocouple, addition funnel and nitrogen bubbler was charged with 425 g (4.88 mol) of (3R)-3-hydroxypyrrolidine, 8 L of dichloromethane, and 1 L (7.17 mol) of triethylamine. The solution was cooled to 5-10° C. with an ice bath and then 1000 g (5.86 mol) of benzyl chloroformate was added dropwise over a period of about 1.5 h keeping the reaction temperature below 20° C. The reaction mixture was stirred for an additional hour in the ice bath, then the bath was removed and the reaction mixture was allowed to warm to ambient temperature overnight. The mixture was poured into a large extractor containing approximately 15 L of saturated aqueous sodium bicarbonate solution. The aqueous phase was back-extracted with two 2-L portions of dichloromethane. The combined organics were-dried over magnesium sulfate and concentrated to give an orange oil. The crude material was taken up in dichloromethane, applied to a 5-kg column of silica gel prepacked in 50% ethyl acetate/hexane, and eluted sequentially with 8 L of 50%, 16 L of 75%, then 100% ethyl acetate/hexane to provide the title compound as a yellow oil which crystallized upon standing.

Step B: Benzyl (3S)-3-fluoropyrrolidine-1-carboxylate

A 5-L, 3-neck, round bottom flask equipped with mechanical stirrer, thermocouple, addition funnel and nitrogen bubbler was charged with 375 mL (2.84 mol) of (diethylamino)sulfur trifluoride and 400 mL of dichloromethane. The solution was cooled to −78° C. To this was added via addition funnel a solution of 304 g (1.37 mol) of benzyl (3R)-3-hydroxypyrrolidine-1-carboxylate in 400 mL of dichloromethane over a 2-h period keeping the reaction temperature below −70° C. The reaction mixture was allowed to stir and warm slowly to ambient temperature overnight. The reaction mixture was added portion-wise with caution to a large extractor containing ice, water, and saturated aqueous sodium bicarbonate solution. The mixture was extracted with 8 L of ethyl acetate. The organic layer was washed with saturated aqueous brine, dried over magnesium sulfate, and concentrated to give a brown oil. Puri- Step C: (3S)-3-Fluoropyrrolidine hydrochloride salt Benzyl (3S)-3-fluoropyrrolidine-1-carboxylate (249 g, 1.11 mmol) was dissolved in 2.3 L of ethanol and then 115 mL of water was added, followed by 30 g of 10% palladium on carbon. The mixture was shaken under 40 psi hydrogen for about 24 h. An additional 10 g and then 5 g of catalyst were added. The mixture was stirred under 40 psi hydrogen gas pressure until complete. The mixture was filtered and the filter cake washed with ethanol. The combined filtrate and washings were treated with 185 mL of concentrated hydrochloric acid and concentrated to a colorless oil. The residue was azeotroped with toluene, then 2 L of diethyl ether was added. Isopropyl alcohol was added until the oil crystallized. The mixture was allowed to age at ambient temperature for 72 h. The crystals were collected, washed with diethyl ether, and dried in vacuo to give the title compound. $[\alpha]_D$=+8.64 (c=4, methanol).

Intermediate 2

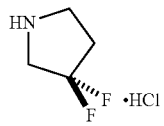

3,3-Difluoropyrrolidine hydrochloride

Step A: Benzyl 3-oxopyrrolidine-1-carboxylate

A 12-L, 3 neck round bottom flask equipped with a mechanical stirrer, thermocouple, condenser, and nitrogen bubbler was charged with 351 g (1.61 mol) of benzyl (3R)-3-hydroxypyrrolidine-1-carboxylate (Intermediate 1, Step A), 6 L of dichloromethane, 500 g of powdered molecular sieves, and 400 g (3.41 mol) of N-methylmorpholine-N-oxide. The resultant suspension was stirred at ambient temperature and to this was added 12.9 g (0.0367 mol) of tetrapropylammonium perruthenate. The reaction temperature was kept at or below 30° C. with a cold water bath. The mixture was stirred at ambient temperature for 2 h. The mixture was poured onto a plug of 5 kg of silica gel and eluted with 10% ethyl acetate/dichloromethane to give the title compound as an orange oil.

Step B: Benzyl 3,3-difluoropyrrolidine-1-carboxylate

A 12-L, 3 neck round bottom flask equipped with a mechanical stirrer, thermocouple, addition funnel and nitrogen bubbler was charged with 292 g (1.33 mol) of benzyl 3-oxopyrrolidine-1-carboxylate and 3 L of dichloromethane. To the stirred solution at ambient temperature was added dropwise 530 mL (4.0 mol) of (diethylamino)sulfur trifluoride over a period of about 3 h, keeping the internal temperature less than 25° C. using a cold water bath. The mixture was stirred at ambient temperature overnight. The mixture was poured into a large extractor containing ice and solid sodium bicarbonate. Eight liters of ethyl acetate were then added and the mixture was made basic with sodium bicarbonate. The organic layer was dried over magnesium sulfate and concentrated to 309 g of a brown oil. Purification by flash chromatography (silica gel, 10 to 20% ethyl acetate/hexane gradient) gave the title compound.

Step C: 3,3-Difluoropyrrolidine hydrochloride

A 242 g (1.00 mol) portion of benzyl 3,3-difluoropyrrolidine-1-carboxylate was converted to the title compound essentially following the procedure outlined in Intermediate 1, Step C. $^1$H NMR (500 MHz, CD$_3$OD): δ 3.7 (t, 2H), 3.6 (t, 21, 2.55 (m, 2H).

Intermediate 3

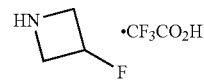

3-Fluoroazetidine trifluoroacetic acid salt

Step A: 1-Benzhydryl-3-fluoroazetidine

A 250 mL, round bottom flask was charged with 3.0 g (12.5 mmol) of 1-benzhydryl-3-hydroxyazetidine and 80 mL of dichloromethane. To the stirring solution at −78° C. was added 4.6 mL (25 mmol) of [bis(2-methoxyethyl)amino]sulfur trifluoride via addition funnel over a period of about 3 h. The reaction mixture was allowed to warm slowly to ambient temperature overnight. The reaction mixture was added portionwise (with caution) to a large extractor containing water and saturated aqueous sodium bicarbonate solution. The mixture was extracted three times with 80 mL of dichloromethane. The combined organic layers were washed sequentially with saturated aqueous sodium bicarbonate solution, water and saturated aqueous brine, dried over sodium sulfate, and concentrated in vacuo. Purification by flash chromatography using a Biotage® system (gradient, hexane to 80% ethyl acetate/hexane) afforded the desired product. LC/MS 242.1 (M+1).

Step B: 3-Fluoroazetidine trifluoroacetic acid salt

1-Benzhydryl-3-fluoroazetidine (1.7 g, 7.04 mmol) was dissolved in 60 mL of ethanol and 500 mg of 20% palladium hydroxide (dry basis) on carbon. The mixture was shaken under 40 psi hydrogen for about 12 h. The mixture was filtered through a Celite pad and the filer cake washed with 100 mL of methanol. The combined washings were treated with 10 mL of trifuoroacetic acid and concentrated to give two oils, the more dense of which is the desired fluoroazetidine salt. The mixture was not purified further. $^1$H NMR (CDCl$_3$) δ 5.45-4.30 (dm, J=56.7 Hz, 1 H), 4.46-4.38 (m, 2 H), 4.24-2.17 (m, 2H).

Intermediate 4

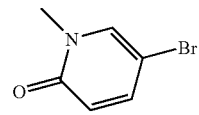

3-Bromo-1-methyl-6-oxo-1,6-dihydropyrdine

Step A: 3-Bromo-6-oxo-1,6-dihydropyridine

A mixture of 5 g of 3-bromo-6-methoxypyridine and 61 g of pyridine hydrochloride was heated at 150° C. for 30 min.

The mixture was poured into saturated aqueous sodium bicarbonate solution and extracted with three portions of 3:1 chloroform/isopropanol solution. The combined organic phases were concentrated to give the title compound, which was used without further purification.

Step B: 3-Bromo-1-methyl-6-oxo-1,6-dihydropyridine

To a solution of 4.38 g of the product from Step A in DMP was added 81 g of cesium carbonate and 30 mL of methyl iodide. The mixture was stirred at ambient temperature overnight, diluted with ethyl acetate, extracted sequentially with two portions of saturated aqueous sodium bicarbonate and brine, dried over sodium sulfate, and concentrated. Purification by HPLC (silica gel, 60% ethyl acetate/hexane) gave the title compound. $^1$H NMR (500 MHz, CDCl$_3$) δ 7.46 (d, 1H, J=2.7 Hz), 7.38 (dd, 1H, J=2.7, 9.8 Hz), 6.52 (d, 1H, J=9.8 Hz), 3.55 (s, 3H).

EXAMPLE 1

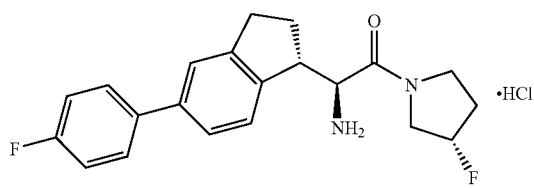

{(1S)-1-[(1S)-5-(4-Fluorophenyl)-2,3-dihydro-1H-inden-1-yl]-2-[(3S)-3-fluoropyrrolidin-1-yl]-2-oxoethyl}amine, hydrochloride Step A: 5-Bromoindan-1-ol To a suspension of 40 g (184 mmol) of 5-bromo-1-indanone in 500 mL of methanol in a water bath was added 16.2 g of sodium borohydride portionwise, keeping the reaction temperature below 40° C. The water bath was removed and the reaction mixture stirred at ambient temperature for 2 h and then quenched by the addition of 100 mL of water. The methanol was removed in vacuo, and the residue partitioned between water and ethyl acetate. The aqueous phase was extracted with two portions of ethyl acetate. The combined organic phases were washed with saturated aqueous sodium chloride solution, dried over sodium sulfate, and concentrated to give a yellow solid which was used without further purification. Mass spectrum (MS): m/z 195, 197 (M+1-H$_2$O), 116 (M+1-H$_2$O-HBr).

Step B: 1,5-Dibromoindane

To a nitrogen-purged flask was added 100 mg (0.469 mmol) of 5-bromoindan-1-ol from Step A and 3 mL of anhydrous chloroform, followed by 0.096 mL (0.704 mmol) of bromotrimethylsilane. The reaction mixture was stirred at ambient temperature overnight and concentrated. The residue was partitioned between ethyl acetate and water. The organic phase was washed with saturated aqueous sodium chloride solution, dried over sodium sulfate, and concentrated to give a brown oil which was used without further purification. Mass spectrum (MS): m/z 195, 197 (M+1-HBr), 116 (M+1-2HBr).

Step C: {(1S)-1-[(1S)-5-Bromo-2,3-dihydro-1H-inden-1-yl]-2-[(3aS,6R,7aR)-(8,8-dimethyl-2,2-dioxidotetrahydro-3a,6-methano-2,1-benzisothiazol-1(4H)-yl]-2-oxoethyl}(diphenylmethylene)amine To a dry, nitrogen-purged flask was added 20.2 g (46.3 mmol) of [2-[(3aS,6R,7aR)-(8,8-dimethyl-2,2-dioxidotetrahydro-3a,6-methano-2,1-benzisothiazol-1(4H)-yl)]-2-oxoethyl](diphenylmethylene)amine [prepared according to the procedure of H. Josien et al., J. Med. Chem., 37, 1586-1601 (1994)] in 200 mL of THF. The mixture was cooled to −78° C. and 43 mL of 1,3-dimethyl-3,4,5,6-tetrahydro-2(1H)-pyrimidinone (DMPU) was added. After 5 min, a solution of n-butyllithium (32 mL, 1.6N in hexane) was added dropwise over 10 min. The mixture was warmed to −20° C., stirred for 20 min, and then cooled to −40° C. A solution of 26 g of 1,5-dibromoindane in 200 mL of THF was added quickly. The mixture was stirred at −15° C. for 1 h and at ambient temperature for 1.5 h, then quenched by the addition of 15 drops of acetic acid and saturated aqueous ammonium chloride solution. The mixture was concentrated. The residue was partitioned between ethyl acetate/ether and saturated aqueous ammonium chloride solution. The organic phase was washed with three portions of saturated aqueous ammonium chloride solution, dried over sodium sulfate, and concentrated to give an oil and solid. The residue was stored in the freezer for several days. The oil/solid mixture was washed sequentially with three portions of ethyl acetate, ether, and petroleum ether and dried in vacuo to give the title compound as a white solid. Mass spectrum (MS): m/z 633 (M+1).

Step D: {(1S)-1-[(1S)-5-Bromo-2,3-dihydro-1H-inden-1-yl]-2-[(3aS,6R,7aR)-(8,8-dimethyl-2,2-dioxidotetrahydro-3a,6-methano-2,1-benzisothiazol-1(4H)-yl)-2-oxoethyl}amine A mixture of 8.35 g (13.2 mmol) of product from Step C in 39.6 mL of 0.5N aqueous hydrochloric acid solution, 28 mL of chloroform, and 20 mL of ether was sonicated for 3 h and then concentrated. The resultant white solid was washed with two portions of ether and dried to give the title compound as its hydrochloride salt. This was partitioned between ethyl acetate/ether and saturated aqueous sodium carbonate. The organic phase was washed with saturated aqueous sodium carbonate, dried over sodium sulfate, and concentrated to give the title compound as a white solid. Mass spectrum (MS): m/z 467, 469 (M+1).

Step E: (2S)-Amino[(1S)-5-bromo-2,3-dihydro-1H-inden-1-yl]acetic acid, hydrochloride A solution of 632 mg of sodium sulfide nonahydrate in 8 mL of water was added to a stirring solution of 800 mg of the compound from Step D in 8 mL of THF at 0° C. After 3.5 h, the mixture was diluted with water and extracted with three portions of chloroform. The aqueous phase was acidified by the addition of 2N hydrochloric acid and concentrated to give the title compound as a white solid. Mass spectrum (MS): m/z 270, 272 (M+1).

Step F: (2S)-[(1S)-5-Bromo-2,3-dihydro-1H-inden-1-yl][(tert-butoxycarbonyl)amino]acetic acid A mixture of 1020 mg of the compound from Step E, 624 mg of sodium bicarbonate, and 464 mg of di-tert-butyl dicarbonate in 20 mL of absolute ethanol was sonicated overnight and then filtered through Celite. The filtrate was concentrated. Purification by flash chromatography (silica gel, eluting with 97:3:0.3, 95:5:0.5 and 90:10:1 dichloromethane:methanol:acetic acid) gave the title compound. Mass spectrum (MS): m/z 392, 394 (M+Na).

Step G: tert-Butyl {(1S)-1-[(1S)-1-[(1S)-5-Bromo-2,3-dihydro-1H-inden-1-yl]-2-[(3S)-3-fluoropyrrolidin-1-yl]-2-oxoethyl}carbamate A mixture of 51 mg of the compound from Step F, 21 mg of (3S)-3-fluoropyrrolidine hydrochloride, 60 mg of O-(7-azabenzotriazol-1-yl)-N,N,N'N'-tetramethyluronium hexafluorophosphate (HATUT), 23 mg of 1-hydroxy-7-azabenzotriazole (HOAt), and 0.07 mL of N,N-diisopropylethylamine in 1 mL of dichloromethane was stirred at ambient temperature for 1 h, and then concentrated. Purification by flash chromatography (silica gel, 0-10% gradient elution then 50% ethyl acetate/hexane) gave the title compound as a yellow semi-solid.

Step H: tert-Butyl {(1S)-1-[(1S)-5-(4-fluorophenyl)-2,3-dihydro-1H-inden-1-yl]-2-[(3S)-3-fluoropyrrolidin-1-yl]-2-oxoethyl}carbamate To a mixture of 25 mg of the product from Step G, 9.2 mg of PdCl$_2$(dppf) and 24 mg of 4-fluorophenylboronic acid in 2 mL of 1:1 ethanol/toluene was added 0.14 mL of 2M aqueous sodium carbonate solution. The reaction mixture was refluxed in a 90° C. bath overnight and then partitioned between ethyl acetate and saturated aqueous sodium bicarbonate solution. The organic phase was washed with brine, dried over sodium sulfate, and concentrated. Purification by HPLC (YMC Pro-C18 column, gradient elution, 20-100% acetonitrile/water with 0.1% TFA) gave the title compound. Mass spectrum (MS): m/z 479 (M+23), 357 (M+1-BOC).

Step I: {(1S)-1-[(1S)-5-(4Fluorophenyl)-2,3-dihydro-1H-inden-1-yl]-2-[(3S)-3-fluoropyrrolidin-1-yl]-2-oxoethyl}amine, hydrochloride A solution of 24.5 mg of the compound from Step H in 1 mL of 4N hydrogen chloride in dioxane was stirred at ambient temperature for 1 h and then concentrated. The resultant solid was washed with ether and dried in vacuo to give the title compound. Mass spectrum (MS): m/z 357 (M+1).

EXAMPLE 2

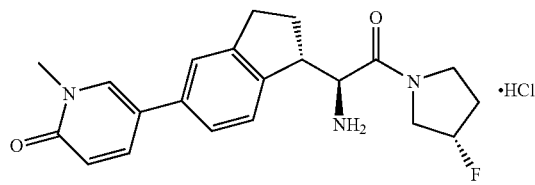

5-((1S)-1-{(1S)-1-amino-2-[(3S)-3-fluoropyrrolidin-1-yl]-2-oxoethyl}-2,3-dihydro-1H-inden-5-yl)-1-methylpyridin-2(1H)-one, hydrochloride Step A: tert-Butyl {(1S)-2-[(3S)-3-fluoropyrrolidin-1-yl]-2-oxo-1-[(1S)-5-(4,4,5,5-tetramethyl-1,3,2-dioxaborolan-2-yl)-2,3-dihydro-1H-inden-1-yl]ethyl}carbamate To a nitrogen-purged flask was added 500 mg of tert-butyl {(1S)-1-[(1S)-5-bromo-2,3-dihydro-1H-inden-1-yl]-2-[(3S)-3-fluoropyrrolidin-1-yl]-2-oxoethyl}carbamate from Example 1 Step G, 441 mg of bis(pinacolato)diboron, 185 mg of PdCl$_2$(dppf), and 336 mg of potassium acetate, followed by 10 mL of DMSO. The mixture was heated at 90° C. for 2.5 h, cooled to ambient temperature, and partitioned between water and 1:1 ethyl acetate/ether. The organic phase was washed with two portions of brine, dried over sodium sulfate, and concentrated. Purification by flash chromatography (silica gel, 5-50% gradient, 50%, then 50-80% gradient ethyl acetate/hexane) gave the title compound.

Step B: tert-Butyl {(1S)-2-[(3S)-3-Fluoropyrrolidin-1-yl]-1-[(1S)-5-(1-methyl-6-oxo-1,6-dihydropyridin-3-yl)-2,3-dihydro-1H-inden-1-yl]-2-oxoethyl}carbamate A mixture of the product from Step A (0.043 mmol), 33 mg of 3-bromo-1-methyl-6-oxo-1,6-dihydropyridine (Intermediate 4), 14 mg of PdCl$_2$(dppf), and 0.22 mg of sodium carbonate in 0.75 mL of DMSO was heated at 80° C. overnight. The mixture was passed through a silica gel plug, washing with ethyl acetate. The filtrate was concentrated. The residue was purified by HPLC (YMC Pro-C18 column, gradient elution, 20-70% acetonitrile/water with 0.1% TEA) to give the title compound. Mass spectrum (MS): m/z 470 (M+1).

Step C: 5-((1S)-{1-(1S)-1-amino-2-[(3S)-3-fluoropyrrolidin-1-yl]-2-oxoethyl}-2,3-dihydro-1H-inden-5-yl)-1-methylpyridin-2(1H)-one, hydrochloride The product from Step B in 1 mL of 4M hydrogen chloride in dioxane was stirred at ambient temperature for 1.5 h and concentrated. The residue was treated with a drop of methanol and then ether. The solid formed was collected, washed with ether, and dried to give the title compound as a solid. Mass spectrum (MS) 370 (M+1).

EXAMPLE 3

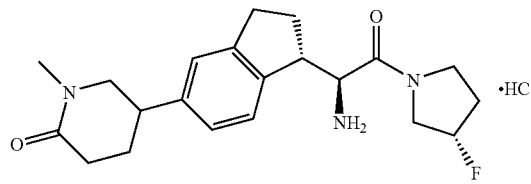

5-((1S)-1-{(1S)-1-Amino-2-[(3S)-3-fluoropyrrolidin-1-yl]-2-oxoethyl}-2,3-dihydro-1H-inden-5-yl)-1-methylpiperidin-2-one hydrochloride A mixture of 144 mg of tert-butyl {(1S)-2-[(3S)-3-fluoropyrrolidin-1-yl]-1-[(1S)-5-(1-methyl-6-oxo-1,6-dihydropyridin-3-yl)-2,3dihydro-1H-inden-1-yl]-2-oxoethyl}carbamate from Example 2 Step B and 10% palladium on carbon in 3 mL of ethanol was treated with hydrogen gas at 50 psi overnight, then filtered and concentrated. Purification by HPLC (Chiralpak AD column, 30% heptane in isopropanol) gave the BOC protected product as two diastereomers. Each diastereomer was treated individually with 1 mL of 4M hydrogen chloride in dioxane for 1.5 h to give two diastereomers of the title compound. Mass spectrum (MS): 374 (M+1).

Essentially following the procedures outlined for Examples 1-3, Examples 4-27 listed in Tables 1 and 2 were prepared.

TABLE 1

| Ex. | R$^4$ | X | MS (M + 1) |
|---|---|---|---|
| 4 | H | (S)—CHF | 263 |
| 5 | Br | (S)—CHF | 341, 343 |

TABLE 1-continued

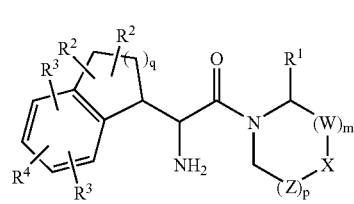

| Ex. | R⁴ | X | MS (M + 1) |
|---|---|---|---|
| 6 | 2-OMe—Ph | (S)—CHF | 369 |
| 7 | [1,2,4]triazolo[1,5-α]pyridin-6-yl | (S)—CHF | 380 |
| 8 | [1,2,4]triazolo[4,3-α]pyridin-6-yl | (S)—CHF | 380 |
| 9 | 3-Cyclopropyl[1,2,4]triazolo[4,3-α]pyridin-6-yl | (S)—CHF | 420 |
| 10 | Br | CF₂ | 359, 361 |
| 11 | 2-(trifluoromethyl)-[1,2,4]triazolo[1,5-α]pyrazin-5-yl | (S)—CHF | 449 |
| 12 | [1,2,4]triazolo[1,5-α]pyrazin-5-yl | (S)—CHF | 381 |
| 13 | 1-methylpyridin-2(1H)-on-5-yl | CF₂ | 388 |
| 14 | 2-(trifluoromethyl)-[1,2,4]triazolo[1,5-α]pyrazin-5-yl | CF₂ | 467 |
| 15 | [1,2,4]triazolo[1,5-α]pyrazin-5-yl | CF₂ | 399 |
| 16 | 1-methylpiperidin-2-on-5-yl | CF₂ | 392 |
| 17 | 1-methylpyrimidin-2(1H)-on-5-yl | (S)—CHF | 371 |

TABLE 2

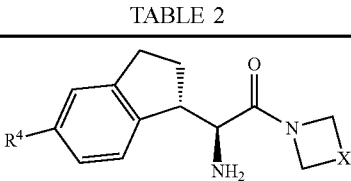

| Ex. | R⁴ | X | MS (M + 1) |
|---|---|---|---|
| 18 | Br | CHF | 327, 329 |
| 19 | 4-F—Ph | CHF | 343 |
| 20 | 1-methylpyridin-2(1H)-on-5-yl | CHF | 456 |
| 21 | [1,2,4]triazolo[4,3-α]pyridin-6-yl | CHF | 366 |
| 22 | [1,2,4]triazolo[1,5-α]pyridin-6-yl | CHF | 366 |
| 23 | [1,2,4]triazolo[1,5-α]pyrazin-5-yl | CHF | 367 |
| 24 | 2-(trifluoromethyl)-[1,2,4]triazolo[1,5-α]pyrazin-5-yl | CHF | 435 |
| 25 | 2-methyl-1,4-dihydro-isoquinolin-3(2H)-on-7-yl | CHF | 408 |
| 26 | 1-methylpiperidin-2-on-5-yl | CHF | 360 |
| 27 | 1-methylpyrimidin-2(1H)-on-5-yl | CHF | 357 |

Example of a Pharmaceutical Formulation

As a specific embodiment of an oral pharmaceutical composition, a 100 mg potency tablet is composed of 100 mg of any of the compounds of the present invention, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

(I)

or a pharmaceutically acceptable salt thereof; wherein
each n is independently 0, 1, or 2;
m and p are each independently 0 or 1;
q is 1 or 2;
X is $CH_2$, S, SO, $SO_2$, CHF, or $CF_2$;
W and Z are each independently $CH_2$, CHF, or $CF_2$;
$R^1$ is hydrogen or cyano;
each $R^2$ is independently selected from the group consisting of hydrogen, halogen, $C_{1-4}$ alkyl, $C_{1-4}$ alkoxy, trifluoromethyl, trifluoromethoxy, and hydroxy;
each $R^3$ is independently selected from the group consisting of hydrogen, halogen, $C_{1-4}$ alkyl, $C_{1-4}$ alkoxy, trifluoromethyl, trifluoromethoxy, and hydroxy;
$R^4$ is hydrogen, halogen, aryl, heteroaryl, or heterocyclyl, wherein aryl, heteroaryl, and heterocyclyl are unsubstituted or substituted with one to five $R^5$ substituents;
each $R^5$ is independently selected from the group consisting of
halogen,
cyano,
oxo,
hydroxy,
$C_{1-6}$ alkyl, wherein alkyl is unsubstituted or substituted with one to five halogens,
$C_{1-6}$ alkoxy, wherein alkoxy is unsubstituted or substituted with one to five halogens,
$(CH_2)_n$—$NR^6R^7$,
$(CH_2)_n$—$CONR^6R^7$,
$(CH_2)_n$—$OCONR^6R^7$,
$(CH_2)_n$—$SO_2NR^6R^7$,
$(CH_2)_n$—$SO_2R^9$,
$(CH_2)_n$—$NR^8SO_2R^9$,
$(CH_2)_n$—$NR^8CONR^6R^7$,
$(CH_2)_n$—$NR^8COR^8$,
$(CH_2)_n$—$NR^8CO_2R^9$,
$(CH_2)_n$—COOH,
$(CH_2)_n$—$COOC_{1-6}$alkyl,
$(CH_2)_n$-aryl, wherein aryl is unsubstituted or substituted with one to five substituents independently selected from halogen, hydroxy, $CO_2H$,
$C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens, (CH$_2$)$_n$-heteroaryl, wherein heteroaryl is unsubstituted or substituted with one to three substituents independently selected from hydroxy, halogen, CO$_2$H, C$_{1-6}$ alkyloxycarbonyl, C$_{1-6}$ alkyl, C$_{3-6}$ cycloalkyl, and C$_{1-6}$ alkoxy, wherein alkyl and alkoxy are unsubstituted or substituted with one to five halogens, (CH$_2$)$_n$-heterocyclyl, wherein heterocyclyl is unsubstituted or substituted with one to three substituents independently selected from oxo, hydroxy, halogen, CO$_2$H, C$_{1-6}$ alkyloxycarbonyl, C$_{1-6}$ alkyl, C$_{3-6}$ cycloalkyl, and C$_{1-6}$ alkoxy, wherein alkyl and alkoxy are unsubstituted or substituted with one to five halogens, (CH$_2$)$_n$—C$_{3-6}$ cycloalkyl, wherein cycloalkyl is unsubstituted or substituted with one to three substituents independently selected from halogen, hydroxy, C$_{1-6}$ alkyl, and C$_{1-6}$ alkoxy, wherein alkyl and alkoxy are unsubstituted or substituted with one to five halogens, wherein any methylene (CH$_2$) carbon atom in R$^5$ is unsubstituted or substituted with one to two groups independently selected from halogen, hydroxy, and C$_{1-4}$ alkyl unsubstituted or substituted with one to five halogens;

R$^6$ and R$^7$ are each independently selected from the group consisting of hydrogen, tetrazolyl, thiazolyl, (CH$_2$)$_n$-phenyl, (CH$_2$)$_n$—C$_{3-6}$ cycloalkyl, and C$_{1-6}$ alkyl, wherein alkyl is unsubstituted or substituted with one to five substituents independently selected from halogen and hydroxy and wherein phenyl and cycloalkyl are unsubstituted or substituted with one to five substituents independently selected from halogen, hydroxy, C$_{1-6}$ alkyl, and C$_{1-6}$ alkoxy, wherein alkyl and alkoxy are unsubstituted or substituted with one to five halogens;

or R$^6$ and R$^7$ together with the nitrogen atom to which they are attached form a heterocyclic ring selected from azetidine, pyrrolidine, piperidine, piperazine, and morpholine wherein said heterocyclic ring is unsubstituted or substituted with one to three substituents independently selected from halogen, hydroxy, C$_{1-6}$ alkyl, and C$_{1-6}$ alkoxy, wherein alkyl and alkoxy are unsubstituted or substituted with one to five halogens; and each R$^9$ is independently selected from the group consisting of tetrazolyl, thiazolyl, (CH$_2$)$_n$-phenyl, (CH$_2$)$_n$—C$_{3-6}$ cycloalkyl, and C$_{1-6}$ alkyl, wherein alkyl is unsubstituted or substituted with one to five halogens and wherein phenyl and cycloalkyl are unsubstituted or substituted with one to five substituents independently selected from halogen, hydroxy, C$_{1-6}$ alkyl, and C$_{1-6}$ alkoxy, wherein alkyl and alkoxy are unsubstituted or substituted with one to five halogens, and wherein any methylene (CH$_2$) carbon atom in R$^9$ is unsubstituted or substituted with one to two groups independently selected from halogen, hydroxy, and C$_{1-4}$ alkyl unsubstituted or substituted with one to five halogens; and each R$^8$ is hydrogen or R$^9$.

2. The compound of claim 1 wherein the carbon atom marked with an * has the stereochemical configuration as depicted in formula Ia:

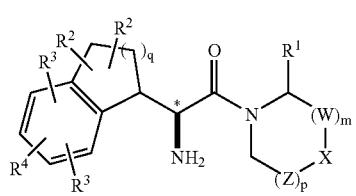

(Ia)

wherein R$^2$ and R$^3$ are each independently hydrogen or fluorine; and

W, X, Z, m, p, q, R$^1$, and R$^4$ are as defined in claim 1.

3. The compound of claim 2 wherein the carbon atom marked with an ** has the stereochemical configuration as depicted in formula Ib:

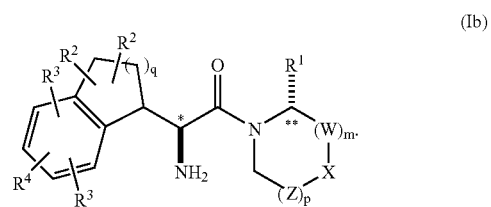

(Ib)

4. The compound of claim 1 wherein m is 1 and p is 0 as depicted in formula Ic:

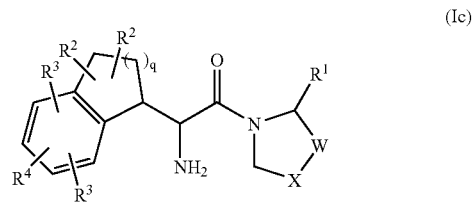

(Ic)

wherein R$^2$ and R$^3$ are independently hydrogen or fluorine, and

W, X, q, R$^1$, and R$^4$ are as defined in claim 1.

5. The compound of claim 4 wherein the carbon atom marked with an * and the carbon atom marked with an ** have the stereochemical configurations as depicted in the formula Id:

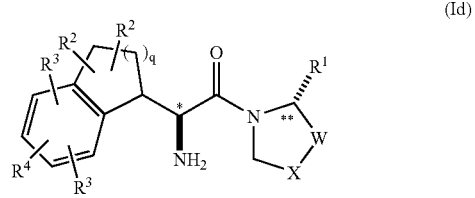

(Id)

wherein R$^2$ and R$^3$ are each independently hydrogen or fluorine.

6. The compound of claim 5 wherein R$^1$ is hydrogen; W is CH$_2$; and X is CH$_2$, CHF or CF$_2$.

7. The compound of claim 1 wherein R$^1$ is hydrogen and m and p are 0 as depicted in the formula Ie:

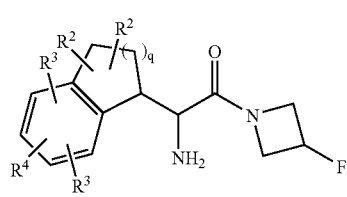

(Ie)

wherein $R^2$ and $R^3$ are each independently hydrogen or fluorine, and q and $R^4$ are as defined in claim 1.

8. The compound of claim 7 wherein the carbon atom marked with an * has the stereochemical configuration as depicted in the formula If:

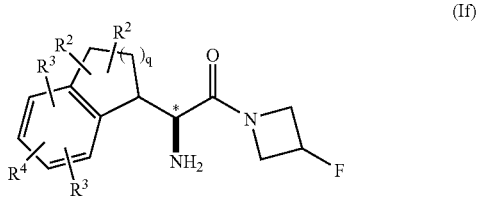

(If)

wherein $R^2$ and $R^3$ are each independently hydrogen or fluorine.

9. The compound of claim 1 of structural formula Ig:

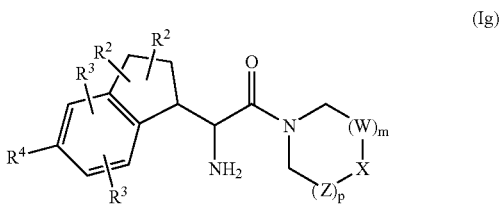

(Ig)

wherein q is 1; $R^2$ and $R^3$ are each independently hydrogen or fluorine; and W, X, Z, m, p, and $R^4$ are as defined in claim 1.

10. The compound of claim 9 wherein the carbon atom marked with an * has the stereochemical configuration as depicted in the formula Ih:

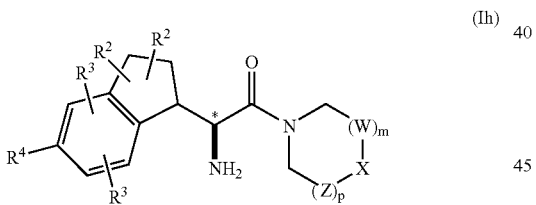

(Ih)

wherein $R^2$ and $R^3$ are each independently hydrogen or fluorine.

11. The compound of claim 9 wherein the carbon atom marked with an * and the carbon atom marked with an *** have the stereochemical configurations as depicted in the formula Ii:

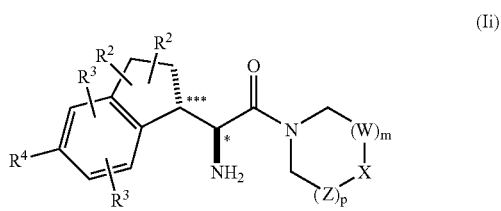

(Ii)

wherein $R^2$ and $R^3$ are each independently hydrogen or fluorine.

12. The compound of claim 11 wherein X is $CH_2$, S, CHF, or $CF_2$;
W and Z are each independently $CH_2$, CHF, or $CF_2$;
$R^4$ is hydrogen, halogen, phenyl, heteroaryl, or heterocyclyl, wherein phenyl, heteroaryl, and heterocyclyl are unsubstituted or substituted with one to three $R^5$ substituents; and
each $R^5$ is independently selected from the group consisting of:
halogen,
cyano,
oxo,
hydroxy,
$C_{1-6}$ alkyl, wherein alkyl is unsubstituted or substituted with one to five halogens,
$C_{1-6}$ alkoxy, wherein alkoxy is unsubstituted or substituted with one to five halogens,
$NR^6R^7$,
$CONR^6R^7$,
$OCONR^6R^7$,
$SO_2NR^6R^7$,
$SO_2R^9$,
$NR^8SO_2R^9$,
$NR^8CONR^6R^7$,
$NR^8COR^8$,
$NR^8CO_2R^9$,
COOH,
$COOC_{1-6}$ alkyl,
aryl, wherein aryl is unsubstituted or substituted with one to five substituents independently selected from halogen, hydroxy, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
heteroaryl, wherein heteroaryl is unsubstituted or substituted with one to three substituents independently selected from hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
heterocyclyl, wherein heterocyclyl is unsubstituted or substituted with one to three substituents independently selected from oxo, hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens, and
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens.

13. The compound of claim 12 wherein each $R^5$ is independently selected from the group consisting of:
halogen,
oxo,
$C_{1-6}$ alkyl, wherein alkyl is unsubstituted or substituted with one to five halogens,
$C_{1-6}$ alkoxy, wherein alkoxy is unsubstituted or substituted with one to five halogens, and
$C_{3-6}$ cycloalkyl.

14. The compound of claim 12 wherein $R^4$ is selected from the group consisting of:
hydrogen,
bromo,
4-fluorophenyl,
2-methoxyphenyl, 1-methylpiperidin-2-on-5-yl,
1-methylpyridin-2(1H)-on-5-yl,
[1,2,4]triazolo[4,3-α]pyridin-6-yl,
3-(cyclopropyl)[1,2,4]triazolo[4,3-α]pyridin-6-yl,
[1,2,4]triazolo[1,5-α]pyridin-6-yl,
[1,2,4]triazolo[1,5-α]pyridin-7-yl,
[1,2,4]triazolo[1,5-α]pyrazin-5-yl,
2-(trifluoromethyl)[1,2,4]triazolo [1,5-α]pyrazin-5-yl, and
1-methylpyrimidin-2(1H)-on-5-yl.

15. The compound of claim 14 of the structural formula selected from the group consisting of:

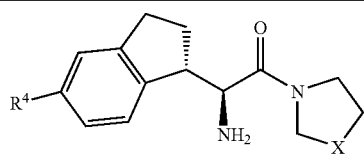

| R⁴ | X |
|---|---|
| H | (S)—CHF |
| Br | (S)—CHF |
| 4-F—Ph | (S)—CHF |
| 2-OMe—Ph | (S)—CHF |
| 1-methylpyridin-2(1H)-on-5-yl | (S)—CHF |
| 1-methyl-piperidin-2-on-5-yl | (S)—CHF |
| [1,2,4]triazolo[1,5-α]pyridin-6-yl | (S)—CHF |
| [1,2,4]triazolo[4,3-α]pyridin-6-yl | (S)—CHF |
| 3-Cyclopropyl[1,2,4]triazolo[4,3-α]pyridin-6-yl | (S)—CHF |
| Br | CF₂ |
| 2-(trifluoromethyl)-[1,2,4]triazolo[1,5-α]pyrazin-5-yl | (S)—CHF |
| [1,2,4]triazolo[1,5-α]pyrazin-5-yl | (S)—CHF |
| 1-methylpyridin-2(1H)-on-5-yl | CF₂ |
| 2-(trifluoromethyl)-[1,2,4]triazolo[1,5-α]pyrazin-5-yl | CF₂ |
| [1,2,4]triazolo[1,5-α]pyrazin-5-yl | CF₂ |
| 1-methylpiperidin-2-on-5-yl | CF₂ |
| 1-methylpyrimidin-2(1H)-on-5-yl | (S)—CHF. |

16. The compound of claim 14 of the structural formula selected from the group consisting of:

| R⁴ | X |
|---|---|
| Br | CHF |
| 4-F—Ph | CHF |
| 1-methylpyridin-2(1H)-on-5-yl | CHF |
| [1,2,4]triazolo[4,3-α]pyridin-6-yl | CHF |
| [1,2,4]triazolo[1,5-α]pyridin-6-yl | CHF |
| [1,2,4]triazolo[1,5-α]pyrazin-5-yl | CHF |
| 2-(trifluoromethyl)-[1,2,4]triazolo[1,5-α]pyrazin-5-yl | CHF |
| 2-methyl-1,4-dihydro-isoquinolin-3(2H)-on-7-yl | CHF |
| 1-methylpiperidin-2-on-5-yl | CHF |
| 1-methylpyrimidin-2(1H)-on-5-yl | CHF. |

17. A pharmaceutical composition which comprises a compound of claim 1 and a pharmaceutically acceptable carrier.

18. A method for treating diabetes in a mammal in need thereof which comprises the administration to the mammal of a therapeutically effective amount of a compound of claim 1.

19. A method for treating non-insulin dependent (Type 2) diabetes in a mammal in need thereof which comprises the administration to the mammal of a therapeutically effective amount of a compound of claim 1.

20. A method for treating hyperglycemia in a mammal in need thereof which comprises the administration to the mammal of a therapeutically effective amount of a compound of claim 1.

* * * * *